United States Patent
Arai et al.

[11] Patent Number: 6,004,299
[45] Date of Patent: *Dec. 21, 1999

[54] INJECTION VESSEL AND SOLUTION-ENCLOSED INJECTION VESSEL IN USE THEREOF

[75] Inventors: Kazuhiko Arai; Tadashi Inoue, both of Oumi-cho, Japan

[73] Assignee: Denki Kagaku Kogyo Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/528,094

[22] Filed: Sep. 14, 1995

[30] Foreign Application Priority Data

Jan. 5, 1995 [JP] Japan .................................. 7-015491

[51] Int. Cl.⁶ .................................................. A61M 5/315
[52] U.S. Cl. ..................... 604/218; 604/111; 604/199; 604/200; 604/241; 604/263
[58] Field of Search ..................................... 604/181, 187, 604/192, 199, 200, 218, 231, 232, 234, 240, 241, 263, 111, 82, 84, 85, 89, 90, 91

[56] References Cited

U.S. PATENT DOCUMENTS

| | | |
|---|---|---|
| 3,989,044 | 11/1976 | Meierhoefer . |
| 4,235,235 | 11/1980 | Bekkering . |
| 4,981,472 | 1/1991 | Ennis, III et al. ..................... 604/239 |
| 5,135,496 | 8/1992 | Vetter et al. .............................. 604/199 |
| 5,419,775 | 5/1995 | Haffner et al. ........................... 604/187 |
| 5,624,405 | 4/1997 | Futagawa et al. ....................... 604/187 |

FOREIGN PATENT DOCUMENTS

| | | |
|---|---|---|
| 0 589 379 | 3/1994 | European Pat. Off. . |
| 2 010 681 | 7/1979 | United Kingdom . |
| 2 040 379 | 8/1980 | United Kingdom . |
| 94/13338 | 6/1994 | WIPO . |
| 9413338 | 6/1994 | WIPO . |

*Primary Examiner*—Ronald K. Stright, Jr.
*Attorney, Agent, or Firm*—Oblon, Spivak, McClelland, Maier & Neustadt, P.C.

[57] ABSTRACT

An injection vessel including a glass cartridge; a rubber stopper (front stopper) and a rubber stopper (end stopper) respectively fitted to a front side and a rear side of the glass cartridge slidably in an axial direction of the glass cartridge in close contact with an inner face of the glass cartridge; a luer lock hub attached to the front end side of the glass cartridge in which a nozzle thereof is protruded outwardly; a finger grip attached to the rear end side of the glass cartridge; a plungerrod for pressing the rubber stopper (end stopper); a nozzle cap covering the nozzle; and wherein a collar consisting of a separate member is protruded equivalently or more than the nozzle or a collar portion with an elevated height attached directly to the luer lock hub is provided at a surrounding of the nozzle of the luer lock hub whereby a front end height of the collar portion is equivalent to or higher than a height of the nozzle.

11 Claims, 2 Drawing Sheets

INJECTION VESSEL AND SOLUTION-ENCLOSED INJECTION VESSEL IN USE THEREOF

The present invention relates to an injection vessel (including not only a general syringe but also a syringe also used as a vessel called a prefilled syringe) and relates to an improved needleless lock type injection vessel.

Further, the present invention relates to an injection vessel wherein a high viscosity solution having the viscosity (limiting viscosity) of 23.6 through 40.7 dl/g, for example, a solution of sodium hyaluronate having an average molecular weight of $1.5 \times 10^6$ through $3 \times 10^6$ which is used in the medical field, is enclosed.

As a system of attaching an injection needle to a nozzle of an injection vessel, there is a type of press-fitting the injection needle into the nozzle by using respective tapers thereof and a lock type wherein in addition to the taper fitting a cylindrical collar portion having a helical screw at the inside thereof is further provided at the outside of the nozzle at the distal end of the cylinder and on the other hand, a flange is provided at the root of the injection needle for screwing to the screw at the inner peripheral face of the collar portion.

The above-mentioned lock type of an injection vessel is selected in cases where high pressure is applied at a fitting portion of the nozzle and the needle root in injection or in case where the injection needle is prevented from dropping off.

A case where a high viscosity solution is injected is assumed to be the case where high pressure is applied on the fitting portion of the nozzle and the needle root. An agent of sodium hyaluronate of high molecular weight provided by microbial fermentation is exemplified as an example of a high viscosity solution.

Hyaluronic acid was separated from a vitreous body of a cattle for the first time and named by Karl Meyer in 1934. Since then the presence has been found in connective tissues of mammals such as umbilical cord, skin, blood vessel, tendon, synovial fluid, cartilage, crista etc. other than the vitreous body of eyes. Further, it is known that it is produced by microorganisms of streptococcus genus which is a kind of lactic acid bacteria.

Hyaluronic acid is a linear anionic polymer having a constituent unit of D-glucuronic acid and N-acetyl-D-glucosamin which is a representative kind of glycosaminoglyca along with chondroitin sulfate, heparin, keratan sulfate and the like.

However, although in other glycosaminoglyca the molecular weight has a comparative low value of several ten thousands or less and the structure is provided with sulfate ester groups, hyaluronic acid is an only macromolecule having no sulfate ester groups and an average molecular weight of 2,000,000 or more.

Accordingly, there is a characteristic difference in comparing physical properties between hyaluronic acid and other proteoglycan in view of high viscoelasticity and water holding property derived therefrom. Further, in a joint it shows a particular viscoelasticity by forming a conjugate with protein or proteoglycan or the like as major components of synovia whereby it is considered that it functions as a lubricant of a joint, a shock absorber against mechanical impact or the like.

Paying attention to such a characteristic Balazs proposed application of hyaluronic acid to articular diseases such as traumatic arthritis, osteoarthritis or the like in 1942. Further, in 1958, he found that hyaluronic acid performs an important operation in maintaining and functioning vitreous tissue after a research on the vitreous bodies of eyes and proposed to use it for replacement of the vitreous solution after an operation for retinal detachment. With this background application of hyaluronic acid to drugs has widely been investigated. As a result it is currently on sale as an assisting agent in ophthalmic operation as well as a remedy for osteoarthritis and frozen shoulder in the orthopedic field.

There are the following problems in the conventional sterilized "needleless lock type injection vessel".

In the conventional injection vessel the height of a collar portion provided externally from a nozzle for fixing an injection needle is set lower than the height of the nozzle. Therefore, sterility is lost when hand, finger or other object is brought into contact with the nozzle in attaching the injection needle at a medical spot and there is a possibility of contamination by microorganisms or viruses.

Especially, in cases where it is injected to an articular cavity or a spinal column, the contamination by microorganisms or viruses gives rise to a serious medical malpractice. Therefore, the contact contamination at the nozzle is severely prohibited and it is the current status that close attention is paid thereto wherein a new injection vessel is always used depending on cases.

In view of the current status, it is an object of the present invention to provide an injection vessel capable of resolving danger of contact contamination in attaching an injection needle while preserving the advantage of the sterilized needleless lock type injection vessel.

Further, many drugs including the exemplified agent of sodium hyaluronate are often supplied in ampules and it is a normal practice when such a drug is supplied in ampules to suck a solution in an ampule by an injection vessel and thereafter inject it in using the drug.

However, in case of a high viscosity solution of sodium hyaluronate having an average molecular weight of 1,500,000 through 3,000,000, with an increase in the concentration, especially the viscosity is enhanced and it is extremely difficult to suck such a solution filled in an ampule by an injection vessel as in a normal injection solution. The difficulty remains the same even in cases where the vessel is changed from an ampule to a vial.

Further, in the operation of cutting an ampule that is a particular problem for an injection agent enclosed in an ampule there is a possibility of mixing glass debris into a solution in cutting the ampule.

In case of the exemplified sodium hyaluronic acid solution Artzdispo (made by Seikagaku Kogyo Co., Ltd.), Healon (made by Pharmacia) and the like are known as injection agents which have previously been filled in injection vessels.

However, in case of Artzdispo filled sodium hyaluronate has a low average molecular weight of 600,000 through 1,200,000, the viscosity is naturally low and also the function of the injection vessel does not correspond to sodium hyaluronate having a high molecular weight. Further, although Healon is provided with sodium hyaluronate having a high molecular weight (1,900,000 through 3,900,000), it is used as an operation assisting agent in the ophthalmic region, the filled amount of sodium hyaluronate is so small as 0.4 ml which is insufficient as an amount of solution used in the orthopedic region. Accordingly, the injection vessel corresponds to the small amount.

As a disposable syringe for filling a solution, a syringe disclosed in Japanese Examined Patent Publication No. 58745/1987 is known. However, it is not manufactured for filling a high viscosity solution and in case where a high viscosity solution including sodium hyaluronate is filled therein, slip or resistant feeling of finger or hand in dosing is unavoidable. Further, it is necessary to pay close attention thereto to prevent contamination by microorganisms or viruses by the contact of hand or finger in attaching an injection needle as in the other disposable syringes.

The inventors have developed an injection vessel comprising as follows to solve the above problems.

According to an aspect of the present invention, there is provided an injection vessel comprising:

a glass cartridge;

a rubber stopper (front stopper) and a rubber stopper (end stopper) respectively fitted to a front side and a rear side of the glass cartridge slidably in an axial direction of the glass cartridge in close contact with an inner face of the glass cartridge;

a luer lock hub attached to the front end side of the glass cartridge in which a nozzle thereof is protruded outwardly;

a finger grip attached to the rear end side of the glass cartridge;

a plungerrod for pressing the rubber stopper (end stopper);

a nozzle cap covering the nozzle; and wherein a collar comprising a separate member is protruded equivalently or more than the nozzle or a collar portion with an elevated height attached directly to the luer lock hub is provided at a surrounding of the nozzle of the luer lock hub whereby a front end height of the collar portion is equivalent to or higher than a height of the nozzle.

According to another aspect of the present invention, there is provided an injection vessel wherein a high viscosity solution having a viscosity (limiting viscosity) of 23.6 through 40.7 dl/g is enclosed in the injection vessel according to the first aspect.

According to another aspect of the present invention, there is provided an injection vessel according to the second aspect, wherein the high viscosity solution is a solution prepared by dissolving sodium hyaluronate having an average molecular weight of $1.5 \times 10^6$ through $3 \times 10^6$ provided by a microbial fermentation into a solvent for injection by a concentration of 0.75 through 1.25 W/V %.

According to the present invention, the collar that is a separate member is provided at the outer periphery of the collar portion or the height of the collar portion is directly heightened whereby the front end height of the collar portion or the collar is set to be equivalent to or higher than that of the front end of the nozzle on the inner side. That is, the nozzle is protected by the outside collar portion or the like. Therefore, it is possible to prevent hands or cloth of an operator from being brought into contact with the front end portion of the nozzle even in a period of time from when the cap is removed to when the injection vessel is attached. Accordingly, the sterility of the nozzle can easily be maintained.

Further, in cases where a high viscosity solution is injected, since the solution has previously been enclosed therein, time and labor of the ampule cutting operation or an operation of sucking a solution into an injection vessel can be saved and the mixing of glass debris into the solution in cutting ampules can be prevented. Further, the operational performance of the injection vessel in which a high viscosity solution such as sodium hyaluronate is enclosed, is not deteriorated in comparison with the conventional injection vessel and contamination by microorganisms or viruses can be prevented thereby providing an enormous advantage.

An explanation will be given of embodiments of the present invention in reference to the drawings as follows.

EXAMPLE 1

Figure 1:
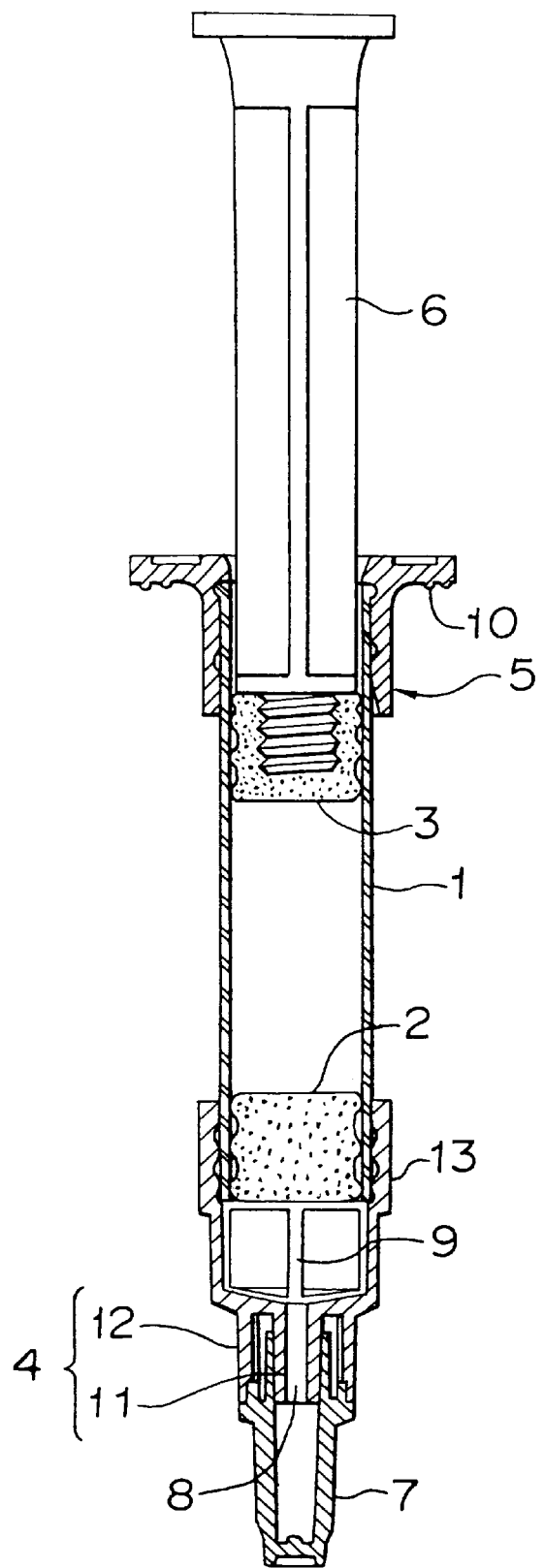
FIG. 1 is a partially broken sectional front view showing an embodiment of the present invention.

As shown in FIG. 1, an injection vessel of the present invention is constituted by a glass cartridge 1, a rubber stopper (front stopper) 2, a rubber stopper (end stopper) 3, a luer lock tip 4, a finger grip 5, a plungerrod 6 and a nozzle cap 7.

The glass cartridge 1 is a transparent glass cylinder and the luer lock tip 4 is attached to the front end side of the cylinder by stopping it by fitting a luer lock hub 13 thereinto. The luer lock tip 4 is made of a transparent synthetic resin and since it is transparent, removal of bubbles in the cylinder particular to a high viscosity injection solution can easily be recognized.

Figure 3:
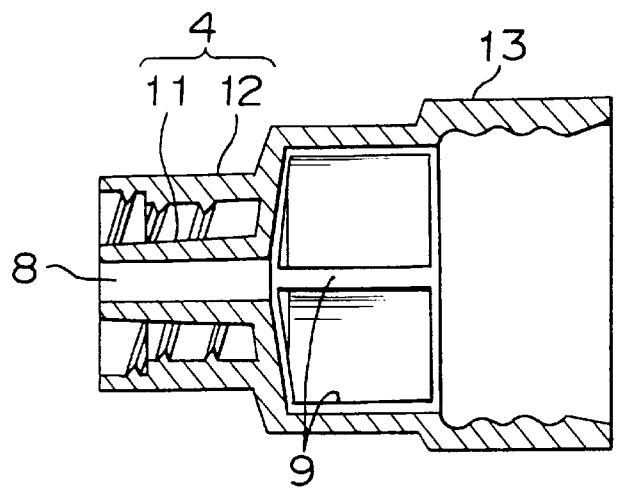
FIG. 3 is a magnified sectional view of a luer lock tip and a luer lock hub.

The luer lock tip 4 and its luer lock hub 13 are shown in FIG. 3 by magnifying them. The luer lock tip 4 is provided with a nozzle 11 protruded outwardly and a collar 12 surrounding the nozzle 11.

The nozzle 11 has a nozzle lumen 8. The collar 12 is provided for protecting the nozzle 11 and is protruded as high as or more than the nozzle 11 by which contamination by microorganisms or viruses by bringing the nozzle 11 in contact with a hand, finger or other object in attaching an injection needle at a medical spot, can be prevented. Further, a screw is formed at an inner peripheral face of the collar 12 for screwing an injection needle (not shown) to be fitted to the nozzle 11.

The luer lock hub 13 has an inner space capable of accommodating the rubber stopper (front stopper) 2 and bypass canals 9 communicating with the nozzle lumen 8 are formed at an inner face thereof.

A nozzle cap 7 is attached to the collar 12 and covers the nozzle 11 whereby contamination of the nozzle 11 before its use can be prevented. The nozzle cap 7 may be fitted to or screwed in the collar 12. Further, in case where the nozzle cap 7 and the collar 12 are partially molten and adhered to each other and the molten and adhered portion is unsealed by cracking it, a syringe that has been recapped after unsealing can easily be identified and malpractice caused by erroneous use of a syringe wherein a period of time has elapsed after unsealing or a used syringe can be prevented which is preferable.

Figure 4:
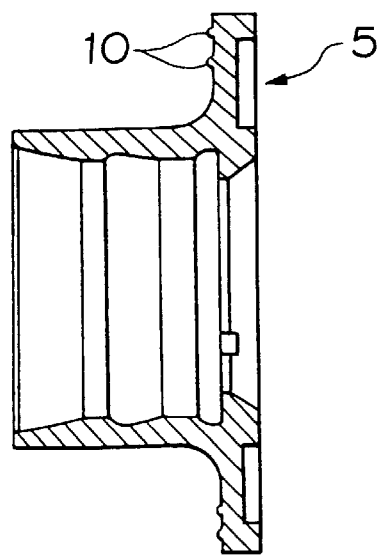
FIG. 4 is a magnified sectional view of a finger grip.

The finger grip 5 is fitted to and stopped by the rear end side of the glass cartridge 1. The finger grip 5 is shown in FIG. 4 by magnifying it wherein a slip preventive working is formed on a face for placing fingers (face on the side of the glass cartridge 1) by providing fine non slip ribs 10. The slip preventive working is carried out to facilitate pressing of the plungerrod 6 in dosing an enclosed solution of sodium hyaluronate.

The rubber stopper (front stopper) 2 is fitted to the inside of the front end side of the glass cartridge 1 in a state slidable in the axial direction in close contact with the inner face of the glass cartridge 1. Meanwhile, the rubber stopper (end stopper) 3 attached to the front end of the plungerrod 6 is fitted from the rear end side of the glass cartridge 1 in close contact with the inner face of the glass cartridge 1. The rubber stopper (end stopper) 3 is slidable in the axial direction in close contact with the inner face of the glass cartridge 1 by pressing the plungerrod 6.

A solution is enclosed between the rubber stopper (front stopper) 2 and the rubber stopper (end stopper) 3.

EXAMPLE 2

An injection vessel in which sodium hyaluronate as an example of a high viscosity solution was enclosed in the injection vessel of Example 1, has been prepared.

The sodium hyaluronate solution is a solution prepared by dissolving sodium hyaluronate having an average molecular weight of 2,030,000 provided by microbial fermentation in a solvent for injection such as water for injection or physiological saline by the concentration of 1.0 W/V %.

The sodium hyaluronate solution enclosed between the rubber stopper (front stopper) 2 and the rubber stopper (end stopper) 3 is dosed by being pushed by pushing the plungerrod 6. When the nozzle cap 7 is removed, an injection needle is attached to the nozzle 11 and the rubber stopper (end stopper) 3 is made to progress by pushing the plungerrod 6 at a medical spot, the rubber stopper (front stopper) 2 is pushed via the sodium hyaluronate solution and the rubber stopper (front stopper) 2 is pushed into the luer lock hub 13. Then, when portions of the bypass canals 9 at the inner face of the luer lock hub 13 are exposed in a region enclosing the sodium hyaluronate solution, the sodium hyaluronate solution is pushed out to the nozzle lumen 8 via the bypass canals 9.

Figure 2:
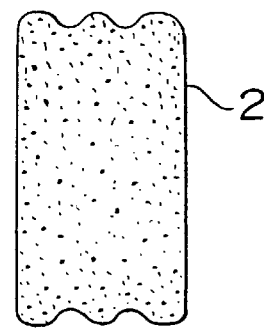
FIG. 2 is a magnified sectional view of a rubber stopper (front stopper)

The rubber stopper (front stopper) 2 is provided with a shape in which corners of outer peripheral edges at both ends thereof are rounded as shown in the magnified sectional view of FIG. 2 to enhance slidability of the rubber stopper (front stopper) 2 and to alleviate burden on hand and finger in dosing the sodium hyaluronate solution. Further, by the same reason the outer peripheral faces of the rubber stopper (front stopper) 2 and the rubber stopper (end stopper) 3 and the inner peripheral face of the glass cartridge 1 are respectively coated by silicone.

A further detailed explanation will be given of embodiments of injection vessels in which sodium hyaluronate is enclosed. However, the present invention is not limited to these embodiments.

EXAMPLE 3

Actual Volume Deviation Test

The actual volume deviation test of the injection vessel of the present invention shown in FIG. 1 through FIG. 4 was carried out according to Japanese Pharmacopoeia, General Rule for Preparation 18, Injection Agent (13). In accordance thereto it is a normal practice that in cases where a solution of a display amount of not less than 2 ml and not more than 5 ml, an excess amount of 0.5 ml is added in cases of a viscous liquid. In case of the injection vessel of the present invention the actual volume deviation test was carried out when an injection agent of 2.75 ml that was a display amount of 2.5 ml plus an excess amount of 0.24 ml was filled and the filling accuracy with regard to the injection vessel that is a constituent element of the present invention was confirmed.

Sodium hyaluronate having an average molecular weight of 2,120,000 obtained by microbial fermentation was dissolved in physiological saline at a concentration of 1.0 W/V %, and 2.75 ml of the solution was filled in an injection vessel as a constituent element of the present invention. Ten such injection vessels were prepared so that they can be distinguished from each other. The injection vessels were dried in a dryer at approximately 60° C. and were cooled in a desiccator as they were. The weight of each of the vessel that was filled with the solution was finely measured. Thereafter, the injection vessels were disintegrated and the solution was washed out. After drying the vacant injection vessels, they were cooled as they were in a desiccator. The weight of each of the vacant vessels was finely measured and the weight of the solution was calculated from the weight of the filled vessel and the weight of the vacant vessel by which the actual volume deviation was calculated for each of them.

The density of sodium hyaluronate is 1.008 and therefore, the weight was converted into the volume by using a density of 1.0. The result is shown in Table 1.

TABLE 1

| Lot number | N | Fill weight (g) | Average actual volume (ml) | Maxima (ml)-Minima (ml) |
| --- | --- | --- | --- | --- |
| 4610-A | 1 | 2.7699 | 2.78 | 2.77–2.79 |
|  | 2 | 2.7860 | (101%) | (101%) (101%) |
|  | 3 | 2.7673 |  |  |
|  | 4 | 2.7724 |  |  |
|  | 5 | 2.7885 |  |  |
|  | 6 | 2.7657 |  |  |
|  | 7 | 2.7701 |  |  |
|  | 8 | 2.7811 |  |  |
|  | 9 | 2.7749 |  |  |
|  | 10 | 2.7857 |  |  |
| 4710-A | 1 | 2.7459 | 2.74 | 2.73–2.75 |
|  | 2 | 2.7468 | (100%) | (99%) (100%) |
|  | 3 | 2.7477 |  |  |
|  | 4 | 2.7459 |  |  |
|  | 5 | 2.7455 |  |  |
|  | 6 | 2.7421 |  |  |
|  | 7 | 2.7464 |  |  |
|  | 8 | 2.7472 |  |  |
|  | 9 | 2.7461 |  |  |
|  | 10 | 2.7303 |  |  |

Japanese Pharmacopoeia prescribes that the average actual volume of 10 samples is not larger than 107% of a sum of the display amount and the excess amount, the actual volume in each injection vessel is not less than the display amount and a number of samples in which the actual volume exceeds 115% of the sum of the display amount and the excess amount is 1 or 0.

From the result of the Example, it was found that the injection vessel of the present invention passed the actual volume deviation test prescribed by the Japanese Pharmacopoeia.

EXAMPLE 4

Solution Discharge Amount Test, Way of Pushing

As in Example 3, sodium hyaluronate having an average molecular weight of 2,210,000 provided by microbial fermentation was dissolved in physiological saline by the concentration of 1.0 W/V % and was filled in each of the injection vessels which are the constituent elements of the present invention by 2.7 ml. A variation due to a difference in a way of pushing the plunger was tested with regard to the discharge amount of the solution from each of the filled injection vessels. An injection needle of 21G11/2 (made by TERUMO CORPORATION) was used.

The test was performed by 3 persons for 10 times wherein the ways of pushing the plunger were changed. The ways of pushing the plunger in 10 times of the test were as follows.

3 Times: Strongly push the plunger until it was stopped;

3 Times: Weakly push the plunger until it was stopped;

4 Times: Push the plunger assuming a normal case of injection.

The result is shown in Table 2.

It was found to be possible that the display amount (2.5 ml) could be discharged with the excess amount of 0.2 ml in either of the ways of pushing the plunger.

TABLE 2

| Tester | Way of pushing | No. of test & discharge amount of solution (g) | | | | Average (g) |
|--------|---------|------|------|------|------|------|
|        |         | 1    | 2    | 3    | 4    |      |
| T.F.   | Strong  | 2.65 | 2.64 | 2.64 |      | 2.64 |
|        | Weak    | 2.54 | 2.52 | 2.52 |      | 2.53 |
|        | Normal  | 2.58 | 2.58 | 2.56 | 2.57 | 2.57 |
| H.S.   | Strong  | 2.64 | 2.65 | 2.63 |      | 2.64 |
|        | Weak    | 2.52 | 2.52 | 2.52 |      | 2.52 |
|        | Normal  | 2.57 | 2.57 | 2.57 | 2.58 | 2.57 |
| R.Y.   | Strong  | 2.63 | 2.63 | 2.64 |      | 2.63 |
|        | Weak    | 2.53 | 2.52 | 2.52 |      | 2.52 |
|        | Normal  | 2.56 | 2.57 | 2.57 | 2.55 | 2.56 |

EXAMPLE 5

Solution Discharge Amount Test, Difference Among Testers

As in Example 3 sodium hyaluronate having an average molecular weight of 2,280,000 provided by microbial fermentation was dissolved in physiological saline by the concentration of 1.0 W/V % and was filled into each of the injection vessels which are the constituent elements of the present invention by 2.7 ml. A variation due to a difference in testers was tested with regard to the discharge amount of the solution from the filled injection vessels. An injection needle of 21G11/2 (made by TERUMO CORPORATION) was used. The test was performed by 10 persons for 3 times.

The test was carried out by assuming a normal injection case with regard to the way of pushing the plunger. The result is shown in Table 3.

TABLE 3

| Tester | No. of test & discharge amount of solution (g) | | | Average (g) |
|--------|------|------|------|------|
|        | 1    | 2    | 3    |      |
| H.I.   | 2.58 | 2.59 | 2.58 | 2.58 |
| T.W.   | 2.56 | 2.58 | 2.58 | 2.57 |
| E.S.   | 2.58 | 2.59 | 2.59 | 2.59 |
| S.S.   | 2.59 | 2.58 | 2.59 | 2.59 |
| Y.S.   | 2.58 | 2.59 | 2.59 | 2.59 |
| R.Y.   | 2.56 | 2.55 | 2.55 | 2.55 |
| M.H.   | 2.59 | 2.58 | 2.60 | 2.59 |
| M.M.   | 2.58 | 2.59 | 2.59 | 2.59 |
| Y.K.   | 2.60 | 2.60 | 2.59 | 2.60 |
| A.W.   | 2.52 | 2.53 | 2.53 | 2.53 |

It was found possible that the display amount (2.5 ml) was discharged with the excess filling amount of 0.2 ml irrespective of the difference in testers.

EXAMPLE 6

Sterility Test

As in Example 3 sodium hyaluronate having an average molecular weight of 1,530,000 provided by microbial fermentation was dissolved in physiological saline by the concentration of 1.0 W/V % and was filled into each of the injection vessels which are the constituent elements of the present invention by 2.7 ml. In a general laboratory assuming a medical spot, an injection needle was attached to each filled injection vessel and thereafter a sterility test was performed with regard to the solution discharged in a clean bench. A needle of 21G11/2 (made by TERUMO CORPORATION) was used. In the sterility test a medium by which a medium function test had been performed was used, incubation was performed by adding a portion of the test solution directly to the medium and the presence or absence of viable cells in the test solution was tested.

In a bacteriological test a thioglycolate medium I for sterility test was used whereas in a mycological test a glucose-peptone medium for sterility test was used. The tests were carried out under conditions of incubation at the temperature of 30 through 32° C. for 7 days for the sterility test and 20 through 25° C. for 10 days for the mycological test. The result is shown in Table 4.

TABLE 4

| Lot number | N | Bacteriological test | Mycological test |
|-----------|---|---------|---------|
| 4610-A    | 1 | Sterile | Sterile |
|           | 2 | Sterile | Sterile |
|           | 3 | Sterile | Sterile |
| 4710-A    | 1 | Sterile | Sterile |
|           | 2 | Sterile | Sterile |
|           | 3 | Sterile | Sterile |
| 4810-A    | 1 | Sterile | Sterile |
|           | 2 | Sterile | Sterile |
|           | 3 | Sterile | Sterile |

The sterility was provided in each of the tests with regard to attaching an injection needle in a general laboratory.

According to the present invention a collar made of a separate member is provided at an outer periphery of a collar portion or the height of the collar portion is increased by which the front end height of the collar portion or the collar is set to be equivalent to or higher than that of the front end of the nozzle, that is, the nozzle is protected by the external collar portion or the like. Therefore, hand or cloth of an operator can be prevented from being brought into contact with the front end portion of the nozzle even in a period of time from when the cap is removed to when the injection vessel is attached. Accordingly, the sterility of a nozzle can easily be maintained.

Further, in case where a high viscosity solution is injected, the solution has previously been enclosed and therefore, time and labor of ampule cutting operation or an operation of sucking the solution into the injection vessel are saved and it is possible to prevent glass debris from mixing into the solution in cutting the ampule. Further, the operational performance of the injection vessel in which a high viscosity solution such as sodium hyaluronate is enclosed is not deteriorated in comparison with the conventional injection vessel and contamination by microorganisms or viruses can be prevented whereby considerable advantage can be provided.

We claim:

1. An injection vessel comprising:
   a glass cartridge;
   a front rubber stopper and a rear rubber stopper respectively fitted to a front end and a rear end of the glass cartridge slidably in an axial direction of the glass cartridge in close contact with an inner face of the glass cartridge;

a high viscosity solution having a limiting viscosity of 23.6 through 40.7 dl/g enclosed in said glass cartridge, between said front rubber stopper and said rear rubber stopper;

a luer lock hub which is fitted to the glass cartridge and which has a luer lock tip attached to the front end of the glass cartridge in which a nozzle is protruded outwardly from the luer lock hub and a collar surrounding the nozzle, said luer lock hub including at least one bypass canal configured so as to communicate said high viscosity solution with said nozzle when said front rubber stopper is positioned proximate to said luer lock tip;

a finger grip attached to the rear side of the glass cartridge;

a plungerrod for pressing the rear rubber stopper;

a nozzle cap covering the nozzle, said nozzle cap being non-hingedly engaged with said collar; and wherein the collar is formed monolithically with the luer lock hub, so that the length of the collar is equivalent to or greater than a length of the nozzle.

2. The injection vessel according to claim 1, wherein the collar of the luer lock hub is made of a transparent resin and the nozzle cap and the collar of the luer lock hub are adhered to each other by partial melting.

3. The injection vessel according to claim 1, wherein the high viscosity solution comprises microbially fermented sodium hyaluronate having an average molecular weight of $1.5 \times 10^6$ through $3 \times 10^6$ dissolved in a saline solvent for injection by a concentration of 0.75 through 1.25 W/V %.

4. An injection vessel comprising:

a glass cartridge;

a front rubber stopper and a rear rubber stopper respectively fitted to a front end and a rear end of the glass cartridge slidably in an axial direction of the glass cartridge in close contact with an inner face of the glass cartridge;

a high viscosity solution having a limiting viscosity of 23.6 through 40.7 dl/g is enclosed in said glass cartridge, between said front rubber stopper and said rear rubber stopper;

a luer lock hub which is fitted to the glass cartridge and which has a luer lock tip attached to the front end of the glass cartridge in which a nozzle is protruded outwardly from the luer lock hub and a collar surrounding the nozzle, said luer lock hub including at least one bypass canal configured so as to communicate said high viscosity solution with said nozzle when said front rubber stopper is positioned proximate to said luer lock tip;

a finger grip attached to the rear side of the glass cartridge;

a plungerrod for pressing the rear rubber stopper;

a nozzle cap covering the nozzle; and wherein the collar is formed monolithically with the luer lock hub, so that the length of the collar is equivalent to or greater than a length of the nozzle;

wherein the collar of the luer lock hub is made of a transparent resin and the nozzle cap and the collar of the luer lock hub are adhered to each other and thereby sealed by partial melting at a joining portion such that said joining portion is changed in appearance when said nozzle cap is subsequently separated from said luer lock hub.

5. An injection vessel comprising:

a cartridge for storing a substance to be injected;

a luer lock hub fitted to said cartridge which has a luer lock tip attached to the front end of the cartridge in which a nozzle is protruded outwardly from the luer lock hub and a collar surrounding the nozzle; and a nozzle cap covering the nozzle;

wherein the collar of the luer lock hub is made of a transparent resin and the nozzle cap and the collar of the luer lock hub are adhered to each other and thereby sealed by partial melting at a joining portion such that said joining portion is changed in appearance when said nozzle cap is subsequently separated from said luer lock hub.

6. The injection vessel according to claim 5, further comprising a front rubber stopper and a rear rubber stopper respectively fitted to a front end and a rear end of said cartridge slidably in an axial direction of said cartridge in close contact with an inner face of said cartridge.

7. The injection vessel according to claim 6, wherein said luer lock hub includes at least one bypass canal configured so as to communicate high viscosity solution stored in said cartridge with said nozzle when said front rubber stopper is positioned proximate to said luer lock tip.

8. The injection vessel according to claim 6, further comprising a plunger rod for pressing the rear rubber stopper.

9. The injection vessel according to claim 5, further comprising a finger grip attached to a rear side of said cartridge.

10. The injection vessel according to claim 5, wherein said collar is formed monolithically with said luer lock hub, so that the length of the collar is equivalent to or greater than a length of said nozzle.

11. The injection vessel according to claim 5, wherein said cartridge is a glass cartridge.

* * * * *